(12) United States Patent
Neto et al.

(10) Patent No.: US 9,249,083 B2
(45) Date of Patent: Feb. 2, 2016

(54) PROCESS FOR SCRUBBING DINITROTOLUENE

(71) Applicant: BASF SE, Ludwigshafen (DE)

(72) Inventors: Samuel Neto, Mannheim (DE); Ruediger Fritz, Bernsdorf (DE); Renate Hempel, Ruhland (DE); Holger Allardt, Schwarzheide (DE); Barbara Becker, Mannheim (DE); Julia Leschinski, Ixelles (BE); Sebastian Ahrens, Wiesloch (DE); Heinrich Hermann, Cologne (DE); Mirko Haendel, Neunkirchen-Seelscheid (DE); Juergen Poehlmann, Cologne (DE)

(73) Assignees: BASF SE, Ludwigshafen (DE); Josef Meissner GmbH & Co. KG, Cologne (DE)

( * ) Notice: Subject to any disclaimer, the term of this patent is extended or adjusted under 35 U.S.C. 154(b) by 273 days.

(21) Appl. No.: 13/870,506

(22) Filed: Apr. 25, 2013

(65) Prior Publication Data

US 2014/0039227 A1 Feb. 6, 2014

Related U.S. Application Data

(60) Provisional application No. 61/637,880, filed on Apr. 25, 2012.

(51) Int. Cl.
| | | |
|---|---|---|
| C07C 205/00 | (2006.01) | |
| C07C 201/00 | (2006.01) | |
| C07C 205/06 | (2006.01) | |
| C07C 201/06 | (2006.01) | |

(52) U.S. Cl.
CPC ............. *C07C 205/06* (2013.01); *C07C 201/06* (2013.01)

(58) Field of Classification Search
CPC .. C07C 205/06; C07C 205/12; C07C 201/06; C07C 201/16
USPC ................................................ 568/924, 927
See application file for complete search history.

(56) References Cited

U.S. PATENT DOCUMENTS

| | | |
|---|---|---|
| 2,976,320 A | 3/1961 | Winstrom et al. |
| 3,742,072 A | 6/1973 | Roth |
| 4,224,249 A | 9/1980 | Kunz et al. |
| 4,361,712 A | 11/1982 | Herman et al. |
| 4,482,769 A | 11/1984 | Toseland et al. |
| 4,597,875 A | 7/1986 | Carr et al. |
| 4,604,214 A | 8/1986 | Carr et al. |
| 4,925,565 A | 5/1990 | Adams et al. |
| 5,356,539 A | 10/1994 | Peter et al. |
| 6,288,289 B1 | 9/2001 | Boyd et al. |
| 6,506,948 B1 | 1/2003 | Sawicki |
| 2007/0088183 A1* | 4/2007 | Hermann et al. ............. 568/927 |

FOREIGN PATENT DOCUMENTS

| | | |
|---|---|---|
| CA | 1 034 603 A1 | 7/1978 |
| CS | 206 757 | 1/1984 |
| DE | 1 221 994 | 7/1966 |
| DE | 1 222 904 | 8/1966 |
| EP | 0 005 203 A2 | 11/1979 |
| EP | 0 279 312 A2 | 8/1988 |
| EP | 0 581 229 A1 | 2/1994 |
| EP | 0 634 365 A1 | 1/1995 |
| EP | 0 736 514 A1 | 10/1996 |
| EP | 0 953 546 A2 | 11/1999 |
| EP | 0 962 446 A1 | 12/1999 |
| EP | 1 003 710 | 5/2000 |
| EP | 1 132 347 A2 | 9/2001 |
| EP | 1 493 730 A1 | 1/2005 |
| EP | 1 496 043 A1 | 1/2005 |
| EP | 1 780 195 A1 | 5/2007 |
| EP | 1 816 117 A1 | 8/2007 |
| IT | 912500 | 3/1972 |
| WO | WO 99/08995 A1 | 2/1999 |

OTHER PUBLICATIONS

U.S. Appl. No. 14/653,687, filed Jun. 18, 2015, Dai, et al.

* cited by examiner

*Primary Examiner* — Jafar Parsa
(74) *Attorney, Agent, or Firm* — Oblon, McClelland, Maier & Neustadt, L.L.P.

(57) ABSTRACT

The invention relates to a process for scrubbing a crude mixture comprising dinitrotoluene, nitric acid, nitrogen oxides and sulfuric acid obtained in the nitration of toluene after the nitrating acid has been separated off, which comprises two scrubbing steps (SS-I) and (SS-II), wherein
  i) in a first scrubbing step (SS-I), the crude mixture is extracted with a scrubbing acid I comprising nitric acid, nitrogen oxides and sulfuric acid in a scrub comprising at least one extraction stage, where the scrubbing acid discharged from the first extraction stage (SS-I-1) of the first scrubbing step (SS-I) has a total acid content of from 20 to 40% by weight and a prescrubbed crude mixture is obtained,
  ii) in a second scrubbing step (SS-II), the prescrubbed crude mixture comprising dinitrotoluene is extracted with a scrubbing acid II in a scrub comprising at least one extraction stage, where the scrubbing acid discharged from the first extraction stage (SS-II-1) of the second scrubbing step (SS-II) has a pH of less than or equal to 4 and a mixture comprising dinitrotoluene which is essentially free of nitric acid, sulfuric acid and nitrogen oxides is obtained.

14 Claims, 2 Drawing Sheets

PROCESS FOR SCRUBBING DINITROTOLUENE

The invention relates to a process for scrubbing a crude mixture comprising dinitrotoluene (DNT), nitric acid, nitrogen oxides and sulfuric acid obtained in the nitration of toluene after the nitrating acid has been separated off.

In particular, the present invention relates to a process for scrubbing the DNT-comprising crude mixture (hereinafter also referred to as crude DNT) from a continuous isothermal nitration of toluene to form DNT in a mixture of sulfuric acid and nitric acid, which allows the resulting scrubbing water from this scrub to be subjected, either directly or after removal of the DNT dissolved in this water by extraction, to biological treatment in a water treatment plant without further physical or chemical pretreatment, where the wastewater running out from the water treatment plant meets the requirements in respect of toxicity as are prescribed, for example, in the wastewater regulations of the Federal Republic of Germany, Appendix 22: Chemische Industrie.

In the continuous isothermal or adiabatic nitration of toluene to form DNT in one or two stages in countercurrent with mixed acid, a crude nitroaromatic product is always obtained after phase separation and this has to be freed of the impurities dissolved therein before further use. Apart from the final nitrating acid composed of nitric acid, sulfuric acid and nitrogen oxides which is present in dissolved form or as microemulsion in the nitroaromatic, oxidation products from secondary reactions with the aromatic to be nitrated, e.g. mononitrocresols, dinitrocresols and trinitrocresols, or aromatic carboxylic acids, e.g. mononitrobenzoic and dinitrobenzoic acids (hereinafter referred to as nitrobenzoic acids or NBA) and degradation products thereof, are also comprised in the crude DNT.

In the prior art, these impurities are removed from the crude product by means of a multistage scrub before the nitroaromatic is passed to a direct use, an isomer separation or a hydrogenation to form the corresponding amines.

The scrub to which the crude nitroaromatic such as DNT is subjected to remove the therein-dissolved and -suspended acids of the nitration mixture, the nitrocresols and other acidic and further impurities which can be extracted by means of the scrubbing medium usually (see, for example, F. Meissner et al in Industrial and Engineering Chemistry Vol 46, 721 (1954), Ullmanns Enzyklopadie der technischen Chemie, 4$^{th}$ edition, Vol. 17, pp. 385-386; H. Hermann et al in ACS-Symposium Series 632, 238 (1996) page 241; ed. L. F. Albright, R. V. C Carr, R. J. Schmitt, U.S. Pat. No. 6,288,289, EP 1 816 117) comprises three steps:

1. a scrub to remove the dissolved and suspended mineral acids such as sulfuric acid, nitric acid and nitrogen oxides (acid scrub);

2. a scrub in the presence of a base (alkali scrub) such as sodium carbonate (soda), sodium bicarbonate, ammonia, sodium hydroxide, potassium hydroxide, etc. (see U.S. Pat. No. 4,482,769, U.S. Pat. No. 4,597,875, U.S. Pat. No. 6,288,289) to remove the weakly acidic impurities dissolved in the crude nitroaromatic, e.g. nitrocresols, nitrobenzoic acids and degradation products from the oxidative degradation of the nitrocresols or of aliphatic or cyclic hydrocarbons, e.g. oxalic acid;

3. a neutral scrub to remove residual traces of alkali and further reduce the impurities remaining in traces in the product. Water is usually used as scrubbing medium for this purpose and the scrub is carried out as a liquid/liquid scrub at the temperatures at which the nitroaromatic to be scrubbed is present as a liquid.

The objective of these scrubs is to obtain not only a pure product but as little as possible wastewater per metric ton of product and to achieve a level of scrubbed-out impurities in the wastewater which enables disposal of said impurities to be carried out inexpensively.

Accordingly, three different wastewater streams are obtained from the scrub of the crude DNT, namely the wastewater from the acid scrub, the alkaline scrub and the neutral scrub.

In the case of DNT, the wastewater from the acid scrub comprises, e.g. when the process described in EP 0 736 514 and EP 1 780 195 is employed, essentially the dissolved product in an amount of up to 0.5% by weight (corresponding to its solubility) together with the mineral acids such as sulfuric acid, nitric acid and nitrous acid dissolved in the crude product in amounts of 25-40% by weight of total acid and only traces of the less acidic nitrophenols, nitrocresols, nitrobenzoic acids or other organic acids such as oxalic acid (from oxidative degradation by nitric acid). The TOC of such wastewater is surprisingly high at about 8-9000 mg/l and less than 50% of it results from the DNT dissolved in the scrubbing acid.

The wastewater from the alkaline scrub has a pH of greater than 9 and comprises, in the case of DNT, about 500-5000 ppm of nitrate, 500-5000 ppm of nitrite and up to a few hundred ppm of sulfate essentially together with up to 1300 ppm of the dissolved product, corresponding to its solubility, the phenolic nitro compounds dissolved in the crude product amounting to up to 800 ppm of nitrocresols, up to 800 ppm of nitrobenzoic acids and traces of cyanide from the oxidative degradation of the nitrocresols in the DNT stage (see U.S. Pat. No. 4,361,712). The TOC in such alkaline scrubbing water from a DNT scrub is 1500-3200 mg/l. Only up to 50% of this TOC results from the nitrocresols and NBA dissolved in the wastewater. The remainder is unknown and probably arises from oxidation products of the nitrocresols in the DNT stage. The alkaline wastewater generally has a deep color ranging from intensive orange to reddish brown.

The wastewater from the neutral scrub can be weakly alkaline or weakly acidic with a pH of 3-8, depending on how much is entrained from the preceding scrubbing stage (the alkaline scrub) and which base was used in the alkaline scrub. Apart from the product which is dissolved to saturation corresponding to its solubility at the scrubbing temperature used, the wastewater from the neutral scrub comprises only residual traces of the base used for the alkaline scrub and the impurities still remaining in the DNT, mainly nitrocresols.

To minimize the amount of water required for this scrub, the scrub is carried out in countercurrent, with the water used for the neutral scrub being employed, after addition of bases, in the alkali scrub (see A. B. Quakenbush et. al., The Olin Dinitrotoluene (DNT) Process, Polyurethane World Congr. Proc. 1993, Publish.: Technomic Lancaster, p. 485) or with the acid scrub being carried out using a minimum amount of water so as to give a concentrated acid which, as described in EP 0 279 312, EP 0 736 514 and EP 1 780 195, can be recirculated directly or after further concentration to the nitration. The vapor condensates obtained in the concentration of scrubbing water are recirculated to the respective scrubs.

Before the wastewater from a plant for the nitration of toluene to form DNT, the scrubbing water from the scrubbing of the crude DNT and the vapor condensates from concentration of the final acids and scrubbing acids can be discharged, they have to be subjected to complicated treatment in order to achieve the applicable discharge parameters as set down in the wastewater regulations of the FRG for, for example, COD, nitrogen, heavy metals and biological parameters before introduction into an outfall drain.

Wastewater streams requiring treatment from nitration plants are the vapor condensate from concentration of the final nitrating acid (referred to as SAC wastewater), which is always acidic, and especially the wastewater from scrubbing with bases, which has a pH in the range 7-10. Before discharge into an outfall drain, all toxic, gene toxic or bacteriostatic substances and also all inorganic salts, especially nitrate and nitrite, have to be removed as far as possible from these wastewater streams in order for the discharge parameters laid down to be met.

The wastewater from the scrubbing of the DNT with bases in particular, which comprises the dissolved product in an amount of up to 0.5%, corresponding to its solubility, together with the phenolic nitro compounds, nitrobenzoic acids and other organic acids and low molecular weight degradation products dissolved in the crude product, requires a high outlay for removal of the toxic, carcinogenic, mutagenic and bacteriostatic nitroaromatics and phenolic and other impurities.

A large number of various methods of removing these toxic substances from the alkaline scrubbing water before discharge have been described.

Apart from purely mechanical separation of the nitrocresols from the wastewater of a DNT scrub by means of bases, preferably sodium carbonate, processes for treatment with activated carbon or ion exchange resins, processes of extraction with the aromatic to be nitrated, treatment with oxidants such as ozone or Fenton's reagent or treatment at high temperatures up to 300° C. have been described, in order to remove or decrease the amount of not only the nitro molecules, predominantly the product, but especially the phenolic nitro molecules such as dinitrophenols and trinitrophenols (picric acid) and dinitrocresols and trinitrocresols (TNCs) from/in the wastewater before this wastewater is passed to subsequent after-treatment in a water treatment plant.

U.S. Pat. No. 4,597,875 describes a process in which the particularly toxic nitrocresols in the wastewater from the scrubbing of DNT by means of sodium carbonate are removed by precipitation. The nitrocresols are concentrated to a content of about 1% of nitrocresol by circulation of the alkaline scrubbing liquor. The nitrocresols are precipitated by subsequent acidification of this concentrated alkaline scrubbing liquor to a pH below 1 by means of sulfuric acid or waste acid and the nitrocresols are separated off and disposed of by incineration. However, this process leads only to a reduction of the toxic substances in the wastewater and not to complete removal of these from the wastewater. In addition, there is a large increase in the content of inorganic salts, so that a wastewater stream which is still polluted with nitrocresols, albeit in a reduced amount, has to be continuously taken off and treated further.

U.S. Pat. No. 4,482,769 describes a further process for reducing the content of nitrocresols in the alkaline scrubbing water from the scrubbing of crude DNT. The trinitrocresols dissolved in the crude DNT are scrubbed out selectively at a pH of about 6 in the alkaline scrubbing liquor while the dinitrocresols remain in the DNT. The burden of toxic nitrocresols in the wastewater to be treated from the DNT scrub is significantly reduced thereby. The dinitrocresols remaining in the DNT do not interfere in the reduction of the DNT to the corresponding amine.

In all these processes, only partial removal of the nitroaromatics and nitrocresols present in the scrubbing water is achieved. This wastewater is therefore still highly polluted after removal of part of the toxic impurities and requires an additional complicated after-treatment before discharge into an outfall drain.

In Chimia 21, 356-360 (1967), R. Angst and M. Brem describe a process for purifying nitrocresol-comprising wastewater from a nitration of toluene to form TNT by treatment with activated carbon. Microbiological purification of the wastewater in combination with in-house wastewater does not bring about, according to these authors, any change in respect of toxicity and color, and the wastewater is successfully decolorized by treatment with activated carbon. A disadvantage of treatment with activated carbon is the high consumption of the latter, since the activated carbon laden with nitroaromatic and nitrocresols cannot be thermally regenerated for safety reasons because of the explosive character of the TNCs and nitroaromatics, or the nitroaromatics can be only partly removed again from the activated carbon by extraction with suitable solvents.

DE 1 221 994 and DE 1 222 904 describe a process for removing the toxic nitrocresols from scrubbing water from a scrub of MNT and DNT, in which the nitrocresols are removed from the wastewater at a pH of greater than 7 by means of strongly basic exchange resins. To regenerate the exchange resin, this is treated with acids and acetone or other suitable solvents. The acetone laden with the nitrocresols is recovered by distillation and the nitrocresols are subsequently destroyed.

A further process described in numerous patents is extraction of the wastewater from the scrub and of the vapor from the concentration of the final acid by means of the aromatic to be nitrated.

U.S. Pat. No. 4,925,565 describes a process for extracting nitrophenol- and/or nitrocresol-comprising wastewater with toluene. At a pH of about 1, the wastewater is virtually completely freed of the nitrophenols in a three-stage countercurrent extraction. The toluene is recovered in a distillation unit and recirculated to the extraction. The mixture of nitroaromatic/nitrocresols obtained at the bottom of the column is incinerated. The wastewater with traces of nitrophenols is, after stripping and before discharge into an outfall drain, subjected to treatment with activated carbon.

U.S. Pat. No. 3,742,072 describes a process in which all neutral nitro molecules, e.g. DNT and TNT, are removed from a "Mahon water" (scrubbing water from the offgas scrub of a TNT plant, specifically an SAC plant) by extraction with toluene and the loaded toluene is recirculated from the extraction to the nitration.

EP 1 003 710 describes a process for extracting the wastewater from the acid scrub of the nitroaromatic, preferably DNT, with the aromatic to be nitrated (toluene) in order to remove the nitroaromatic dissolved in this acidic scrubbing water before this wastewater is subjected to further treatment, e.g. concentration. The extractant loaded with the extracted nitroaromatic is recirculated to the nitration.

U.S. Pat. No. 6,506,948 describes a process by means of which the neutral nitro molecules, e.g. the DNT, are selectively separated off by extraction of the individual wastewaters from a plant for preparing DNT (vapor condensate, acidic and finally alkaline wastewater) with toluene in countercurrent and are recirculated with the toluene to the nitration. The wastewater which now only comprises the nitrocresols is subjected to further degradation to remove the nitrocresols, in which the neutral nitro molecules no longer interfere.

IT 912500 and CS 206 757 describe a process by means of which not only the neutral nitroaromatics such as DNT and MNT but also the nitrocresols are removed from the combined scrubbing water from the scrubbing of the nitroaromatic by extraction with the aromatic to be nitrated at pH values of less than 5. These nitrophenols are obtained as highly concentrated solution by back extraction from the extractant with alkali and the nitrophenols are separated off from this solution after acidification and passed to incineration. The extractant, viz. the aromatic to be nitrated, with the extracted DNT is recirculated to the nitration.

EP 1 493 730 and EP 1 496 043 likewise describe a process for the partial purification of combined wastewater from the preparation of DNT, comprising the wastewater from the acid scrub and the alkaline scrub of the DNT and the vapor condensate from the concentration of the MNT final acid having a content of MNT/DNT of 0.7-13%. The pH of this combined wastewater should be less than 5 as a result of a suitable combination of the various wastewater streams. Up to 90% of the nitrocresols and nitrobenzoic acids suspended in the combined wastewater are extracted by the MNT/DNT phase which separates out from the vapor condensate from the SAC plant in a separator. The MNT/DNT mixture having a content of nitrocresols and nitrobenzoic acids of, for example, 13.8% by weight which separates out is either disposed of by incineration or the nitrocresols are degraded oxidatively by means of a mixed acid suitable for this purpose (EP 1 493 730). The wastewater obtained after the MNT/DNT phase has been separated off can be extracted further with toluene, with the MNT and DNT still dissolved in the combined wastewater and a further proportion of the nitrocresols still dissolved in the wastewater being removed therefrom. The toluene extract is recirculated to the nitration. The partially purified wastewater obtained after the extraction with toluene, which can still comprise a maximum of 200 ppm of nitrocresols, cannot be discharged directly but has to be treated further before discharge into an outfall drain.

All these processes, enrichment of the pollutants present in the wastewater and subsequent disposal of these combined with only partial removal of the impurities from the individual or combined wastewater streams from the DNT scrub are technically complicated, require additional chemicals and lead, as a result of the acidification of the alkaline scrubbing liquor and the back neutralization to a pH of about 7, to an additional salt burden in the wastewater.

To avoid these technically complicated enrichment technologies, processes have been developed which dispose of the pollutants, especially the nitrocresols, by chemical degradation without intermediate enrichment in the individual or combined wastewater streams.

EP 0 962 446 describes a process for the partial removal of nitroaromatics and nitrocresols dissolved in the alkaline wastewater by oxidation by means of nitric acid. The presence of not more than 4% by weight of nitric acid and up to 4% by weight of sulfuric acid at a pH of less than 3 and subsequent heating to up to 180° C. results in degradation of a considerable part of the nitrocresols and the dissolved DNT in an originally alkaline wastewater from the scrubbing of the DNT. The TOC of the alkaline wastewater is reduced by up to 50%. The resulting, partially purified wastewater has to be passed to further treatment, e.g. treatment with activated carbon or biological treatment.

U.S. Pat. No. 4,604,214 and U.S. Pat. No. 5,356,539 describe a process in which the nitrocresols dissolved in the alkaline scrubbing water from scrubbing of DNT are degraded by means of hydrogen peroxide in the presence of iron(II) salts (Fenton's reagent). The nitrocresols are enriched to a content of about 1% by weight by multiple circulation of the alkaline scrubbing water. To treat this alkaline scrubbing water, it is acidified to a pH of less than 4.5, preferably 3, admixed with a sufficient amount of hydrogen peroxide (7-12 mol/mol of TNC) and iron salts and degraded at a temperature of 70-90° C. More than 90% of the nitrocresols and about 50% of the dissolved DNT are degraded at an average residence time of about 45 minutes in a continuous reactor. Here too, only partial purification of the alkaline scrubbing water occurs. The residual content of nitrocresols in the wastewater which has been treated in this way, which is up to 200 ppm, has to be reduced by means of further measures, e.g. treatment with activated carbon, to such an extent that discharge into an outfall drain is possible according to applicable present-day standards.

Apart from oxidation by means of hydrogen peroxide, ozone has also been used in a targeted manner as oxidant for the degradation of nitrocresols in alkaline scrubbing water from a DNT plant.

EP 0 634 365 describes the use of ozone after removal of the neutral nitro molecules from the alkaline nitrophenol-comprising scrubbing water of a nitrobenzene plant. EP 0 953 546, paragraph 0007, describes a combination process comprising adsorption of water treatment sludge for the partial removal of DNT, biological pretreatment, ozonization and biological after-treatment of nitrocresol-comprising wastewater from a DNT plant. The DNT laden water treatment sludge is incinerated.

Although no complicated intermediate concentration of the toxic constituents from the alkaline scrub of a crude DNT, e.g. the nitroaromatic and nitrocresols, is necessary before disposal thereof when oxidants such as nitric acid, hydrogen peroxide or ozone are used, the additional consumption of oxidants in combination with complicated biological intermediate purification and final purification steps is complicated, burdensome and expensive.

EP 0 581 229 describes a wet oxidation of alkaline wastewater which still comprises all nitro molecules and nitrocresols from a DNT scrub, in the presence of an additional oxidant such as oxygen or air below the supercritical temperature range for water at 325-370° C. but at a supercritical pressure of 220-325 bar, in which the oxidant is completely in solution in the wastewater and the salts (carbonates) present in the wastewater and formed by the oxidation remain dissolved and are not precipitated by evaporation reactions (and thus hinder the thermolysis). The residence times necessary for oxidative degradation are short. The wastewater is still yellow-colored after a thermolysis in the presence of oxidant and has to be after-treated before discharge into an outfall drain.

To avoid intermediate purification steps and additional consumption of expensive auxiliaries such as acids, bases and oxidants in the removal of nitro molecules and nitrophenols which cannot be biodegraded in wastewater from the preparation of DNT, processes by means of which these disadvantages, especially the additional consumption of auxiliaries, can be avoided have been additionally described.

EP 0 005 203 describes a thermolysis process for the direct treatment of alkaline wastewater comprising nitrocresols from a nitration plant for preparing DNT, for which no additional chemicals nor other intermediate steps are required. The wastewater from the alkaline scrubbing stage of a DNT plant, free of the neutral nitroaromatics such as DNT, is treated directly for 15 minutes at 290-300° C. and a pressure of about 100-110 bar, with exclusion of air and oxygen. After cooling to room temperature, all sodium salts of the nitrocresols have been decomposed into $CO_2$, CO, nitrogen and other short-chain degradation products of the nitrocresols.

EP 0 953 546 describes a process which even allows the thermolysis to be carried out in the presence of the neutral nitro molecules such as DNT in the wastewater from an alkaline scrubbing stage of a DNT plant. The complicated removal of the nitroaromatics which do not have a hydroxy group, e.g. the nitrotoluenes or dinitrotoluenes, by extraction or steam stripping before introduction into the thermolysis is dispensed with.

EP 1 132 347 describes a thermolysis in the supercritical range for a preconcentrated alkaline scrubbing water from the scrubbing of nitrobenzene. The preconcentration separates off the major part of the steam-volatile nitroaromatics dissolved in the scrubbing water, in the present case nitrobenzene, from the scrubbing water. Only the nitrophenols dissolved as salts remain and are completely degraded at 500-600° C. and 25 MPa (250 bar). The distillate from the preconcentration is recirculated to the scrub. The wastewater from the thermolysis comprises only small amounts of organic impurities and can be after-treated in a water treatment plant.

The alkaline wastewater streams from scrubbing of DNT in the alkaline scrubbing stage are, after leaving the thermolysis, generally free of nitrocresols and DNT but sometimes have a deep color due to colloidally precipitated carbon and comprise, apart from low molecular weight degradation products of unknown constitution derived from DNT and the nitrocresols, ammonia, freshly formed sodium carbonate and traces of dissolved CO. Compared to the untreated water, the TOC has been reduced by about 20% and the COD by about 30-35% in the thermolysis. It is surprising that mononitroaromatics such as MNT are degraded significantly more slowly than the dinitroaromatics and trinitroaromatics and the nitrobenzoic acids are virtually not degraded at all under the conditions of the thermolysis and remain unchanged in the wastewater. This wastewater from the thermolysis therefore has to be after-treated, e.g. in a water treatment plant, to adhere to the applicable regulations in respect of color, COD, TOC and toxicity before discharge into an outfall drain.

The treatment in a thermolysis of wastewater which comprises neutral nitroaromatics such as DNT and even more toxic nitrophenols and nitrocresols and cannot be biodegraded or can be biodegraded only with difficulty is very effective but technically complicated and expensive.

All processes, apparatuses and measures described above for the treatment of wastewater from the preparation of DNT, in particular the wastewater which is polluted with the toxic and difficult or impossible to degrade nitrocresols from the scrubbing of DNT by means of alkalis, comprise two stages, namely a) the removal of the DNT dissolved in the water and the toxic nitrocresols as far as possible, b) the after-treatment of the wastewater which has been prepurified according to a), e.g. in a water treatment plant or by treatment with adsorbents, before ultimate discharge into an outfall drain.

All these processes and apparatuses for treatment of this wastewater polluted with nitro molecules, especially the pretreatment according to a), are technically complicated and expensive in terms of capital cost and operation, require additional chemicals and sometimes lead to additional pollution with inorganic salts which are introduced into the wastewater to be treated by the acidification and the subsequent neutralization. In addition, mixing of the alkaline wastewater from the DNT scrub with acids for the purpose of separating off the nitrocresols at pH values of less than 5 leads to the evolution of considerable amounts of $CO_2$, which leads to problems owing to vigorous foaming thereof combined with considerable offgas pollution.

In addition, processes have also been described in which, in order to reduce the pollution of the wastewater from the scrubbing of crude DNT with toxic nitrocresols, part of the nitrocresols and nitrophenols remains in the product (DNT) and is separated off and disposed of together with the "heavy ends" only after hydrogenation of the DNT to form diaminotoluene (TDA).

U.S. Pat. No. 2,976,320 and U.S. Pat. No. 4,482,769 describe processes in which only part of the nitrocresols and nitrophenols present in the crude DNT remain in the DNT (max 500 ppm, preferably not more than 200 ppm). This results in wastewater from the scrub which also comprises the major part of the "nitrophenols" present in the crude DNT. This wastewater has to be, according to the prior art, treated further before discharge into an outfall drain.

CA 1 034 603 describes a process in which the crude DNT is scrubbed only with water in order to remove the mineral acids, which have an adverse effect on the hydrogenation, as completely as possible (at least 99.8%). Part of the nitrocresols dissolved in the crude DNT remains in the DNT and is separated off at the TDA stage. Up to almost 40% of the nitracresols originally present in the crude DNT go into the wastewater. In addition, all of the mineral acids originally present in the crude DNT are dissolved in this wastewater. Especially the nitrate but also the remaining nitrocresols have to be removed from this scrubbing water in a complicated manner according to the prior art before this scrubbing water is discharged into the outfall drain.

U.S. Pat. No. 4,224,249 describes a process for hydrogenating DNT which has been only incompletely scrubbed with water and comprises residual acid (up to 6000 ppm as sulfuric acid or 7700 ppm as nitric acid) using Raney nickel to form diaminotoluene (TDA). However, as the examples show, the activity of the catalyst is reduced to zero after only a short time at a residual acidity of about 6000 ppm in the scrubbed DNT in the presence of about 800 ppm of nitrocresols. In addition, about one third of the "nitrophenols" originally present in the crude DNT go into the scrubbing water in the scrub, which is not described in more detail, and have to be removed in a complicated manner according to the above-described prior art before the scrubbing water is discharged into the outfall drain.

It is an object of the invention to provide a process for scrubbing the dinitrotoluene-comprising crude mixture obtained in the nitration of toluene after the nitrating acid has been separated off, which allows the wastewater from this scrub to be discharged directly and without complicated intermediate treatment to separate off or destroy the nitrocresols and nitrobenzoic acids into the biological treatment stage of a water treatment plant. The wastewater treated in the biological stage should be able to be introduced into an outfall drain while adhering to all relevant legal requirements, e.g. the provisions of the wastewater discharge regulations of the Federal Republic of Germany. In particular, it is an object of the invention to provide a process for scrubbing the DNT-comprising crude mixture, in which the nitrobenzoic acids (mononitrobenzoic and dinitrobenzoic acids) present in the DNT-comprising crude mixture do not get into the wastewater from the scrub. A further object of the invention is to provide a process of this type in which the content of nitric acid and sulfuric acid in the DNT-comprising crude mixture is minimized and at the same time pollution of the wastewater with sulfate and nitrate is minimized. A further object of the invention is to provide a process of this type wherein, after the scrubbing, "technical grade DNT" is obtained in which the known degradation products and potential catalyst poisons stemming from the oxidative degradation at the DNT stage of the nitration, which may interfere with the catalytic reduction of DNT with hydrogen, such as hydrocyanic acid (HCN), nitrous oxide ($N_2O$), nitrogen oxides (NOx) and carbon monoxide (CO), are minimized.

The object is achieved by a process for scrubbing a crude mixture comprising dinitrotoluene, nitric acid, nitrogen oxides and sulfuric acid obtained in the nitration of toluene after the nitrating acid has been separated off, which comprises two scrubbing steps (SS-I) and (SS-II), wherein i) in a first scrubbing step (SS-I), the crude mixture is extracted with a scrubbing acid I comprising nitric acid, nitrogen oxides and sulfuric acid in a scrub comprising at least one extraction stage, where the scrubbing acid discharged from the first extraction stage (SS-I-1) of the first scrubbing step (SS-I) has a total acid content of from 20 to 40% by weight and a prescrubbed, dinitrotoluene-comprising crude mixture is obtained, ii) in a second scrubbing step (SS-II), the prescrubbed crude mixture is extracted with a scrubbing acid II in a scrub comprising at least one extraction stage, where the scrubbing acid discharged from the first extraction stage (SS-II-1) of the second scrubbing step (SS-II) has a pH of less than or equal to 4 and a mixture comprising dinitrotoluene which is essentially free of nitric acid and sulfuric acid is obtained.

The crude mixture may additionally contain traces of hydrocyanic acid, nitrous oxide and carbon monoxide.

It has surprisingly been found that the acid scrub according to the invention comprising a first scrubbing step (SS-I) and a second scrubbing step (SS-II) gives, in the second scrubbing step, wastewater which can be introduced without intermediate treatment for separating off nitrocresols (dinitrocresols and trinitrocresols) and nitrobenzoic acids (mononitrobenzoic and dinitrobenzoic acids) and also oxidative degradation products of the dinitrocresols into the biological treatment stage of a water treatment plant. The wastewater obtained after leaving the biological treatment stage can be discharged directly and with adherence to the limit values prescribed in relevant wastewater regulations, for example those of the Federal Republic of Germany, into an outfall drain. In particular, it was surprising that when the pH value is adhered to in the first extraction stage of the second scrubbing step, virtually the entire amount of the nitrobenzoic acids remains in the DNT-comprising organic phase and does not go over into the wastewater.

At the same time, the pollution of the wastewater with sulfate and especially with nitrate, which can be removed only with difficulty from the wastewater, is significantly reduced compared to the prior art as described, for example, in U.S. Pat. No. 2,976,320, U.S. Pat. No. 4,482,769 and CA 1 034 603.

The process of the invention represents a further development of the best available technologies (BAT), as listed in the BREFs (BAT reference document), in the sense of the EU Directive on the integrated reduction and avoidance of environmental pollution (IRE-D). The process of the invention not only enables the total amount of wastewater from a DNT plant to be significantly reduced but the comprehensive and technically complicated measures for the removal or partial removal of the nitrocresols, nitrobenzoic acids and other degradation products from the wastewater can also be dispensed with.

In the first scrubbing step (SS-I) of this process, the mineral acids sulfuric acid and nitric acid and also nitrogen oxides dissolved in the DNT-comprising crude mixture are separated off in an at least one-stage extraction using a scrubbing acid as extractant.

The first scrubbing step is preferably carried out in at least two stages and in countercurrent. The at least two-stage countercurrent extraction can in principle be carried out as described in EP 0 279 312, EP 0 736 514 or EP 1 780 195.

In countercurrent, the second scrubbing step is generally carried out as follows:

I) in the first extraction stage (SS-I-1) of the first scrubbing step (SS-I), the crude mixture comprising dinitrotoluene, nitric acid, nitrogen oxides and sulfuric acid is fed into a first mixer (M-I-1) together with circulated scrubbing acid (SA-I-1) from a first phase separation apparatus (S-I-1) belonging to this first extraction stage and excess scrubbing acid (SA-I-2) from the subsequent extraction stage (SS-I-2), the scrubbing emulsion formed in the mixer is separated in the first phase separation apparatus (S-I-1) into the scrubbing acid (SA-I-1) and crude mixture which has been scrubbed once (DNT-I-1) and II) the crude mixture which has been scrubbed once (DNT-I-1) is, in the subsequent extraction stage (SS-I-2) of the first scrubbing step (SS-I), fed into a second mixer (M-I-2) belonging to this extraction stage together with the circulated scrubbing acid (SA-I-2) from a second phase separation apparatus (S-I-2) belonging to this extraction stage and, if the first scrubbing step (SS-I) comprises more than 2 extraction stages, with excess scrubbing acid (SA-I-3) from the subsequent extraction stage (SS-I-3) or, if the first scrubbing step comprises precisely 2 extraction stages, with fresh water or scrubbing acid, where, if the first scrubbing step comprises more than 2 extraction stages, further extraction steps corresponding to the steps I) and II) can follow.

The countercurrent extraction can have up to n extraction stages. Here, the extractant is fed into the last of the n extraction stages (SS-I-n) of the first scrubbing step (SS-I). The introduced extractant which is fed into this last extraction stage can be fresh water or a scrubbing acid having a particular total acid content. In an embodiment of the invention, the extractant introduced is water. In a further embodiment, the extractant introduced is a scrubbing acid having a total acid content in the range from 0.2 to 1.5% by weight. For example, this scrubbing acid can be the vapor condensate from the concentration of the scrubbing acid obtained in the first extraction step (SS-I-1) of the first scrubbing stage (SS-I). This generally comprises up to 1.0% by weight of nitric acid and up to 0.3% by weight of sulfuric acid.

The scrubbing acid obtained in the first scrubbing step in the first extraction stage generally has a total acid content of from 20 to 40% by weight. This total acid content is the sum of nitric acid, sulfuric acid and nitrogen oxides, with nitrogen oxides being calculated as nitrous acid $HNO_2$.

The scrubbing acid obtained in the first scrubbing step at the first extraction stage can be recirculated either directly or after being concentrated to the nitration of toluene. It can also be introduced into the concentration of the final acid from the first stage of the toluene nitration (mononitrotoluene (MNT) stage). In this first scrubbing step (SS-I), the loading of the wastewater obtained in the second scrubbing step with sulfate and nitrate is essentially minimum. The nitrate can be removed from the wastewater only by means of a complicated denitrification stage.

The prescrubbed, DNT-comprising crude mixture obtained after the first scrubbing step generally has a content of sulfate of not more than 300 ppm, preferably not more than 100 ppm and particularly preferably not more than 50 ppm, and a content of nitric acid and nitrogen oxides of not more than 5000 ppm, preferably not more than 3000 ppm and particularly preferably not more than 1000 ppm.

In the second scrubbing step (SS-II), the remaining residues of nitric acid, nitrogen oxides and sulfuric acid are scrubbed out from the prescrubbed, DNT-comprising crude mixture by means of an at least one-stage extraction with a scrubbing acid which has only a low content of total acid (essentially nitric acid, nitrogen oxides and sulfuric acid) so that the content of mineral acids and nitrogen oxides in the DNT-comprising crude mixture is reduced to a minimum.

The second scrubbing step is preferably carried out in at least two stages and in countercurrent. The countercurrent extraction can have up to m extraction stages. Here, the extractant is fed to the last of the m extraction stages (SS-II-m) of the second scrubbing step (SS-II). The extractant introduced is generally fresh water.

In countercurrent, the second scrubbing step is generally carried out as follows:

I) in the first extraction stage (SS-II-1) of the second scrubbing step (SS-II), the prescrubbed crude mixture comprising dinitrotoluene is fed into a first mixer (M-II-1) belonging to this extraction stage together with circulated scrubbing acid (SA-II-1) from a first phase separation apparatus (S-II-1) belonging to this extraction stage and excess scrubbing acid (SA-II-2) from the subsequent extraction stage (SS-II-2), the scrubbing emulsion formed in the first mixer is separated in the first phase separation apparatus (S-II-1) into the scrubbing acid (SA-II-1) and crude mixture which has been scrubbed once (DNT-II-1) and II) the crude mixture which has been scrubbed once (DNT-II-1) is, in the subsequent extraction stage (SS-II-2) of the second scrubbing step (SS-II), fed into a second mixer (M-II-2) belonging to this extraction stage together with the circulated scrubbing acid (SA-II-2) from a second phase separation apparatus (S-II-2) belonging to this second extraction stage and, if the second scrubbing step (SS-II) comprises more than 2 extraction stages, with excess scrubbing acid (SA-I-3) from the subsequent extraction stage (SS-I-3) or, if the scrubbing step comprises precisely 2 extraction stages, with fresh water, where, if the second scrubbing step comprises more than 2 extraction stages, further extraction steps corresponding to the steps I) and II) can follow. Here, the second scrubbing step is carried out so that essentially the total amount of nitrocresols and nitrophenols and preferably up to 95% by weight of the nitrobenzoic acids originally present in the crude mixture remain in the crude mixture and are not discharged with the scrubbing acid. This is achieved according to the invention by the scrubbing acid discharged from the first extraction stage (SS-II-1) of the second scrubbing step (SS-II) having a pH of less than or equal to 4. In the low-concentration scrubbing acid having a pH of 4 or less which is discharged as wastewater, the total content of nitrocresols and nitrophenols is generally less than 5 ppm and the content of nitrobenzoic acids is generally less than 50 ppm. This wastewater, which now only comprises the scrubbed DNT in dissolved form up to the saturation limit, can be fed to a water treatment plant without the pretreatment hitherto customary and required to remove the nitrocresols and nitrobenzoic acids and also toxic oxidative degradation products, either directly or after recovery of the dissolved DNT.

In each of the two scrubbing steps (SS-I) and (SS-II), scrubbing is preferably carried out in at least two stages in countercurrent. In one embodiment, the first scrubbing step (SS-I) comprises from 2 to 4 extraction stages (n=2-4). In a further embodiment, the second scrubbing step (SS-II) comprises from 2 to 4 extraction stages (m=2-4). It is also possible to provide more extraction stages, for example 5 or 6, per scrubbing step. In one embodiment, each scrubbing step comprises precisely 2 extraction stages.

The amount of extractant or fresh water to be added in the last extraction stage of each scrubbing step depends on the total acid content (SS-I) or the pH(SS-II) wanted in the first extraction stage of the respective scrubbing step (SS-I) or (SS-II).

The volume ratio of DNT-comprising crude mixture (organic phase) to scrubbing acid (aqueous phase) which are in direct contact with one another in each scrubbing apparatus is generally selected in the range from 1:4 to 10:1, preferably from 1:3 to 5:1 and particularly preferably from 1:3 to 2:1, in both scrubbing steps. Depending on the phase ratio and energy input during dispersion, the mixture can be present as an oil-in-water emulsion (O/W emulsion) or as a water-in-oil emulsion (W/O emulsion).

These phase ratios can be set by introduction of the appropriate amount of extractant into the last extraction stage, but preferably, at a defined amount of extractant, by circulation of the scrubbing acid after phase separation, with only the excess (corresponding to the amount of extractant freshly introduced in the last extraction stage) being introduced into or discharged from the preceding extraction stage.

The pH of the scrubbing acid taken off from the first extraction stage (SS-II-1) of the first scrubbing step (SS-II) is generally in the range from 0 to 3, preferably from 0.5 to 2 and particularly preferably from 0.8 to 1.2. The desired, optimal pH in the first extraction stage of the second scrubbing step can be set via the residual content of nitric acid in the prescrubbed crude mixture originating from the first scrubbing step and/or via the amount of fresh water introduced into the last extraction stage of the second scrubbing step. As an alternative, the desired pH can also be set by addition of a mineral acid, for example the scrubbing acid from the first scrubbing step, or of sulfuric acid or preferably nitric acid.

The ratio of DNT to fresh water which is introduced into the last extraction stage of the second scrubbing step can, on a volume basis, be varied in the range from 1:2 to 15:1, corresponding to from 1.5 $m^3$ to 0.05 $m^3$ of fresh water per t of DNT, preferably from 1:1 to 7:1, corresponding to from 0.75 $m^3$ to 0.107 $m^3$ of fresh water per t of DNT, and particularly preferably from 1:1 to 2:1, corresponding to from 0.75 $m^3$ to 0.38 $m^3$ of fresh water per t of DNT. Both washing steps are carried out at a temperature above the melting point of DNT, generally at 60-75° C.

As scrubbing apparatuses for both scrubbing steps, it is possible to use, for example, mixer-settler apparatuses or stirred multistage or pulsed packed columns or sieve tray columns, and also static mixers in combination with suitable separation apparatuses. Both static separators and dynamic separators (centrifugal separators) are suitable for separation of the scrubbing dispersion composed of DNT-comprising crude mixture to be scrubbed and scrubbing acid.

The scrubbing acid discharged from the first extraction stage (SS-II-1) of the second scrubbing step (SS-II), which has a pH of less than or equal to 4, preferably from 0 to 3, particularly preferably from 0.5 to 2 and in particular from 0.8 to 1.2, generally has a content of sulfate of not more than 100 ppm, a content of nitric acid of not more than 2000 ppm and a content of $HNO_2$ of not more than 50 ppm. In addition, it comprises isomeric dinitrotoluenes in an amount corresponding to the saturation limit at the given temperature, for example from 800 to 1000 ppm. The content of nitrocresols and nitrophenols is generally less than 1 ppm, and the content of nitrobenzoic acids is generally less than 50 ppm.

The TOC (total organic carbon) content of this wastewater is, for example, only about 1100 mg/l, compared to about 3000 mg/l in wastewater from the alkaline DNT scrub using sodium carbonate. This COD (chemical oxygen demand) of this wastewater is, for example, only about 3000 mg O/l, compared to about 6000 mg O/l in wastewater from the alkaline DNT scrub using sodium carbonate. This wastewater can be passed, either directly or after recovery of the dissolved DNT by extraction with toluene, without further pretreatment such as thermolysis or treatment with oxidants, to the biological treatment stage of a water treatment plant and then generally meets all requirements of the wastewater regulations of the Federal Republic of Germany in respect of toxicity including gene toxicity, determined in accordance with DIN EN ISO 38415 T6 (fish), 11348-2 (luminous bacteria), 38412 L30 (daphnia), 38412 L33 (algae) and DIN EN ISO 9888 (Umu Test, gene toxicity).

In general, the scrubbing acid discharged from the first extraction stage (SS-II-1) of the second scrubbing step (SS-II) is neutralized and can, optionally after removal of dinitrotoluene dissolved therein by extraction and removal of the extractant, be fed without further pretreatment to the biological treatment stage of a water treatment plant.

A DNT which has a residual acidity of generally not more than 300 ppm (determined as sulfuric acid) and a pH of 2-4 and generally comprises not more than 800 ppm of nitrocresols and nitrophenols, not more than 600 ppm of nitrobenzoic acids (dinitrobenzoic and mononitrobenzoic acids) and a residual content of generally not more than 300 ppm, preferably not more than 200 ppm, and particularly preferably not more than 100 ppm of nitric acid (NOx, determined as nitric acid), not more than 50 ppm, preferably not more than 10 ppm, and particularly preferably not more than 1 ppm of hydrocyanic acid, not more than 200 ppm, preferably not more than 50 ppm, and particularly preferably not more than 25 ppm of nitrous oxide, not more than 400 ppm, preferably not more than 200 ppm, and particularly preferably not more than 50 ppm of CO, and not more than 3 ppm of sulfate, is taken off from the last extraction stage of the second scrubbing step (SS-II). This DNT and the nitrocresols, nitrophenols, nitrobenzoic acids and traces of NOx, hydrocyanic acid, nitrous oxide and CO dissolved therein can be hydrogenated completely and without problems in a manner corresponding to the prior art to form toluenediamine (TDA) and the corresponding aminocresols, aminophenols and aminobenzoic acids (diaminobenzoic and monoaminobenzoic acids). The aminocresols, aminophenols and aminobenzoic acids remain in the distillation residue in the TDA distillation and are disposed of together with this.

A further advantage is the greater thermal stability of the DNT which has been subjected according to the invention to an acid scrub. Thus, the temperature at which thermal decomposition commences is increased by about 20° C. in the case of a DNT which has been subjected only to an acid scrub and comprises, for example, 620 ppm of nitrophenols and nitrocresols and 460 ppm of nitrobenzoic acids compared to a DNT which has been scrubbed in accordance with the prior art in the presence of sodium carbonate and comprises, for example, less than 20 ppm of nitrophenols and nitrocresols.

Figure 1:
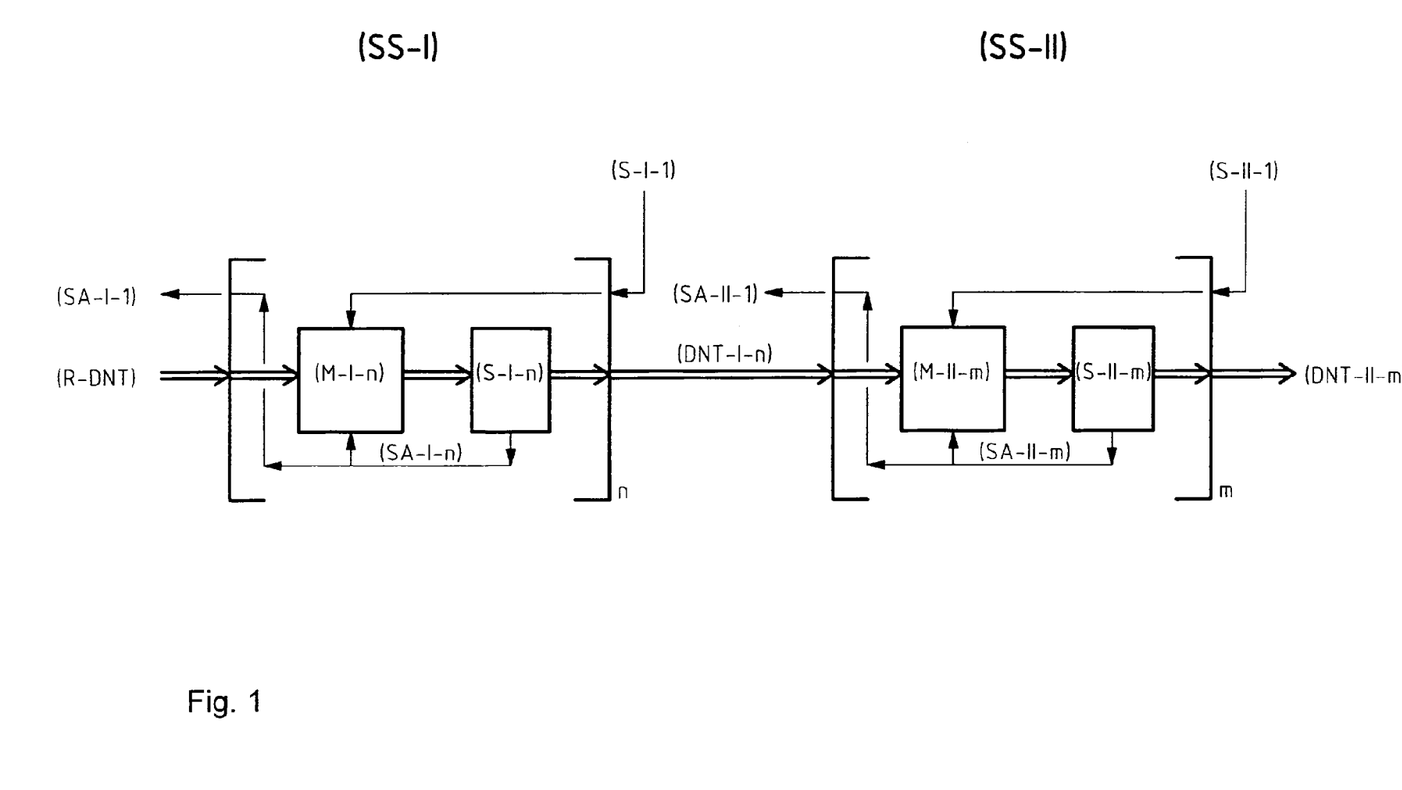
FIG. 1 shows a scrub of crude DNT by the process of the invention according to a preferred embodiment of the invention.

FIG. 1 schematically shows a scrub of crude DNT by the process of the invention according to a preferred embodiment of the invention.

The crude DNT (C-DNT) from the nitration after removal of the DNT final acid is, in scrubbing step I (SS-I), fed into the mixer (M-I-1) of the first extraction stage (SS-I-1) (n=1) together with the circulated scrubbing acid (SA-I-1) from the phase separation apparatus (S-I-1) together with the excess scrubbing acid (SA-I-2) from the subsequent extraction stage (SS-I-2) in such a way that the prescribed phase ratio of scrubbing acid to DNT is established. After phase separation of the scrubbing emulsion in the phase separation apparatus (S-I-1) belonging to the extraction stage, the scrubbing acid (SA-I-1) which has been separated off is recirculated to the mixer (M-I-1) belonging to this stage. The excess scrubbing acid (SA-I-1) is recirculated either directly or after concentration to the nitration.

The once-scrubbed DNT (DNT-I-1) separated off in the separator (S-I-1) is fed into the mixer (M-I-2) of the subsequent extraction stage (SS-I-2) (n=2) together with the circulated scrubbing acid (SA-I-2) from the phase separation apparatus (S-I-2) together with the excess scrubbing acid (SA-I-3) from the subsequent extraction stage (SS-I-3) so that the prescribed phase ratio of scrubbing acid to DNT is established. After phase separation of the scrubbing emulsion in the phase separation apparatus (S-I-2) belonging to this extraction stage, the scrubbing acid (SA-I-2) which has been separated off is recirculated to the mixer (M-I-2) belonging to this stage. The excess scrubbing acid (SA-I-2) is fed into the preceding extraction stage (SS-I-1). The twice-scrubbed DNT (DNT-I-2) separated off in the phase separation apparatus (S-I-2) is transferred to the next extraction stage (SS-I-3) (n=3) for a third scrub. The number of extraction stages can preferably be up to four (n=4). Fresh water or preferably the vapor condensate from concentration of the scrubbing acid from the scrubbing stage (SS-I-1) is fed as scrubbing medium (S-I-1) into the last extraction stage (SS-I-4) in such an amount that the scrubbing acid separated off from (S-I-1) has a total acid content of 20-40%.

The prescrubbed DNT (DNT-I-n) from scrubbing step (SS-I) is, in scrubbing step (SS-II), fed into the mixer (M-II-1) of the first extraction stage (SS-II-1) (m=1) together with the circulated scrubbing acid (SA-II-1) from the phase separation apparatus (S-II-1) together with the excess scrubbing acid (SA-II-2) from the subsequent extraction stage (SS-II-2) in such a way that the prescribed phase ratio of scrubbing acid to DNT is established. After phase separation of the scrubbing emulsion in the phase separation apparatus (S-II-1) belonging to the scrubbing stage, the scrubbing acid (SA-II-1) which has been separated off is recirculated to the mixer (M-II-1) belonging to this stage. The excess scrubbing acid (SA-II-1) is fed, either directly or after recovery of the product (DNT) dissolved therein, to a final biological after-treatment.

The once-scrubbed DNT (DNT-II-1) separated off in the phase separation apparatus (S-II-1) is fed into the mixer (M-II-2) of the subsequent extraction stage (SS-II-2) (m=2) together with the circulated scrubbing acid (SA-II-2) from the phase separation apparatus (S-II-2) and the excess scrubbing acid (SA-II-3) from the subsequent scrubbing stage (SS-II-3) in such a way that the prescribed phase ratio of scrubbing acid to DNT is established. After phase separation of the scrubbing emulsion in the phase separation apparatus (S-II-2) belonging to this extraction stage, the scrubbing acid (SA-II-2) which has been separated off is recirculated to the mixer (M-II-2) belonging to this stage. The excess scrubbing acid (SA-II-2) is fed into the preceding extraction stage (SS-II-1). The twice-scrubbed DNT (DNT-II-2) separated off in the phase separation apparatus (S-II-2) is transferred to the next extraction stage (SS-II-3) (m=3) for a third scrub. The number of extraction stages can preferably be up to four (m=4). Fresh water is fed as scrubbing medium (S-II-1) into the last extraction stage (SS-II-4) in such an amount that the scrubbing acid separated off from (S-II-1) has a pH of preferably 0-3. The pH in the first scrubbing stage (SS-II-1) can additionally be readjusted to the optimal operating value by addition of nitric acid or scrubbing acid (SA-I-1).

Figure 2:
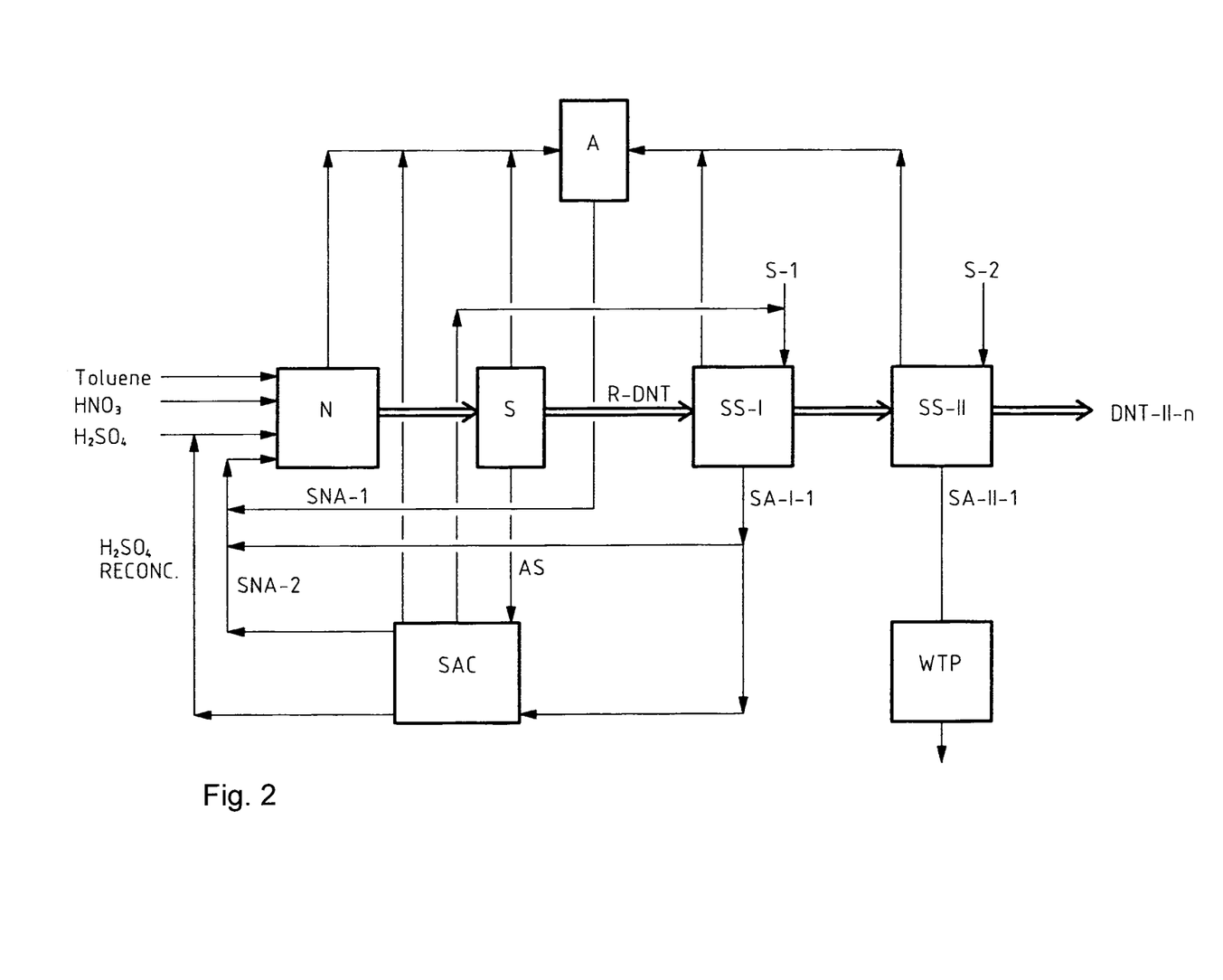
FIG. 2 shows a production plant according to the invention for the nitration of toluene to form DNT with subsequent scrubbing according to the invention of the crude DNT in two steps according to a preferred embodiment of the invention.

FIG. 2 schematically shows a production plant according to the invention for the nitration of toluene to form DNT with subsequent scrubbing according to the invention of the crude DNT in two steps according to a preferred embodiment of the invention.

The dinitrotoluene isomer mixture formed by means of a two-stage continuous isothermal or adiabatic nitration of toluene in countercurrent with a mixture of sulfuric acid and nitric acid in the nitration unit (N) is, after separation of the nitration emulsion in the phase separation apparatus (separator (S)), fed to a scrub according to the invention having two scrubbing steps (SS-I) and (SS-II). In scrubbing step (SS-I), the mineral acids sulfuric acid, nitric acid and nitrogen oxides dissolved in the crude DNT are scrubbed out. The scrubbing acid (SA-I-1) separated off from the first scrubbing stage (SS-I-1) in this scrubbing step, which has a total acid content of 20-40% by weight, is recirculated directly to the nitration unit (N) or after further concentration as (SNA-2) to the nitration. The vapor condense from concentration of the scrubbing acid (SA-I-1) and/or the final nitrating acid is recirculated as scrubbing water (W-1) to the scrubbing step (SS-I).

In the second scrubbing step (SS-II), the residues of mineral acids still remaining in the prescrubbed DNT from (SS-I) are scrubbed out in such a way that a scrubbing acid (SA-II-1) having a pH in the range of preferably 0-3 results. To supplement the amount of scrubbing acid separated off, fresh water is added in (SS-II). This scrubbing acid from scrubbing step II (SS-II) is brought to a pH of 6-8 and then subjected directly or after recovery of the DNT dissolved therein to a biological after-treatment in a water treatment plant (WTP).

The final nitrating acid obtained in the separation unit (S) is reconcentrated to give sulfuric acid (up to 96%) in a concentration plant for sulfuric acid (SAC) and recirculated to the nitration. The nitric acid (SNA-1) recovered in the offgas treatment (OT) from the collected offgases comprising nitrogen oxides from nitration and scrubbing is recirculated together with the scrubbing acid (SA-I-1) obtained from scrubbing step (SS-I) or, after concentation, as (SNA-2) to the nitration.

The present invention is illustrated by the following example.

EXAMPLES

Example 1

Prior Art 4500 kg/h of DNT having a residual content of 0.94% by weight of sulfuric acid, 1.43% by weight of nitric acid and 1.15% by weight of nitrogen dioxide were, after removal of the final nitrating acid, scrubbed in countercurrent in 2 stages in an acid scrub (scrubbing step I). In the first extraction stage, scrubbing was carried out using a scrubbing acid comprising 7.58% by weight of sulfuric acid, 19.52% by weight of nitric acid and about 0.45% by weight of nitrogen oxides (as $HNO_2$) at a phase ratio of DNT to scrubbing acid of 1:1. In the second extraction stage of scrubbing step I, scrubbing was carried out using a scrubbing acid comprising a maximum of 0.5% by weight of sulfuric acid, about 6% by weight of nitric acid and about 0.15% by weight of nitrogen oxides, likewise at a phase ratio of 1:1. The amount of added water or condensate from the further concentration of the scrubbing acid (in the present example about 450 l/h) fed into the last extraction stage is selected so that the concentration of the scrubbing acid which is in contact with the crude DNT to be scrubbed in the first extraction stage of the acid scrub does not exceed the laid-down acid strength and density. To maintain the prescribed phase ratio, the scrubbing acid separated off in the separator (phase separation apparatus) of the respective extraction stage was circulated and only the excess was transferred or discharged into the preceding scrubbing stage.

The scrubbing acid having a total acid content of 27.55 40% by weight discharged from the acid scrub was, after further concentration, recirculated to the nitration.

The DNT from the acid scrub, which was virtually free of the mineral acids, was freed of residues of the scrubbing acid still dissolved or entrained in the prescrubbed DNT and the nitrophenols and nitrocresols in the alkaline scrub.

About 4350 kg of prescrubbed DNT from scrubbing step I (acid scrub) having a residual content of not more than 100 ppm of sulfuric acid and not more than 3000 ppm of nitric acid/nitrogen oxides were scrubbed in a phase ratio of 1:1 in one stage in the presence of a base (sodium carbonate) in an alkaline scrubbing step (alkali scrub), with a pH of 9-10 being established. After phase separation of the scrubbing emulsion from the alkali scrub, the DNT which had been separated off was scrubbed, likewise in a phase ratio of 1:1, to remove the entrained traces from the alkali scrub by addition of fresh water in a single-stage neutral scrub. After phase separation, the scrubbing water separated off in the neutral scrub was fed as scrubbing water into the alkali scrub. To maintain the prescribed phase ratios in the two scrubbing steps (alkali scrub and neutral scrub), the scrubbing water separated off in the separator of the respective scrubbing stage was circulated and only the excess was transferred from the neutral scrub to the alkali scrub or discharged from the alkali scrub.

The alkaline scrubbing liquor discharged from the alkali scrub, which had a pH of 9-10, a content of 40 ppm of sulfate, 580 ppm of nitrate, 2500 ppm of nitrite, 990 ppm of DNT and 740 ppm of trinitrocresols, was fed directly to a thermolysis at 290° C. and 90 bar in order to degrade the nitrophenols and nitrocresols and also further nitro compounds and the dissolved DNT. The water running out from the thermolysis, in which the nitrophenols and nitrocresols and the dissolved DNT had been destroyed, was subjected to a biological after-treatment in a water treatment plant before discharge into the outfall drain.

Example 2

According to the Invention 4500 kg/h of DNT having a residual content of 0.94% by weight of sulfuric acid, 1.43% by weight of nitric acid and 1.15% by weight of nitrogen dioxide were, after removal of the final nitrating acid, scrubbed in countercurrent in 2 stages in the scrubbing step I (SS-I). In the first extraction stage (SS-I-1), scrubbing was carried out using a scrubbing acid comprising 7.58% by weight of sulfuric acid, 19.52% by weight of nitric acid and about 0.45% by weight of nitrogen oxides (as $HNO_2$) at a phase ratio of DNT to scrubbing acid of 1:1. In the second extraction stage (SS-I-2) of scrubbing step I, scrubbing was carried out using a scrubbing acid comprising a maximum of 0.5% by weight of sulfuric acid, about 6% by weight of nitric acid and about 0.15% by weight of nitrogen oxides, likewise at a phase ratio of 1:1. The amount of added water or condensate from the further concentration of the scrubbing acid (in the present example about 450 l/h) fed into the last extraction stage is selected so that the concentration of the scrubbing acid which is in contact with the crude DNT to be scrubbed in the first extraction stage (SS-I-1) does not exceed the laid-down acid strength and density. To maintain the prescribed phase ratio, the scrubbing acid separated off in the separator (phase separation apparatus) of the respective extraction stage was circulated and only the excess was transferred or discharged into the preceding scrubbing stage.

The scrubbing acid having a total acid content of 27.55% by weight discharged in the scrubbing step (SS-I) was, after further concentration, recirculated to the nitration.

The prescrubbed DNT which had been virtually completely freed of the mineral acids in scrubbing step (SS-I) was freed of residues of the scrubbing acid from scrubbing step I (SS-I) still dissolved or entrained in the DNT in scrubbing step II (SS-II).

About 4350 kg of prescrubbed DNT from scrubbing step I (SS-I) having a residual content of not more than 100 ppm of sulfuric acid and not more than 2000 ppm of nitric acid/nitrogen oxides were scrubbed in countercurrent in two stages. In the first extraction stage of scrubbing step II (SS-II), scrubbing was carried out using a scrubbing acid having a pH of 0-3, particularly preferably 0.8-1.2, at a phase ratio of DNT:scrubbing acid of 1:2. In the second extraction stage of scrubbing step II (SS-II), scrubbing was carried out using a scrubbing acid which comprised only traces of mineral acid, especially nitric acid, likewise in a phase ratio of 1:2. The amount of added fresh water (in the present example about 2000 l/h) which was fed to the last extraction stage (SS-II-n) (n=2) was selected so that the pH in the first extraction stage (SS-II-1) in which the DNT from the scrubbing step I (SS-I) is extracted was kept at the laid-down optimal value in the range 0.8-1.2. To maintain the prescribed phase ratios in the extraction stages, the scrubbing acid separated off in the separator of the respective extraction stage was circulated and only the excess was transferred or discharged into the preceding stage.

The scrubbing acid discharged from the first extraction stage (SS-II-1) in scrubbing step II (SS-II), which had a pH of 1.0, a content of 85 ppm of sulfuric acid, 1800 ppm of nitric acid, 40 ppm of nitrogen oxides, 980 ppm of DNT, less than 1 ppm of trinitrocresols and less than 10 ppm of nitrobenzoic acids, was fed directly to a biological treatment. The wastewater obtained after this biological treatment met all requirements in respect of toxicity laid down in the wastewater regulations of the Federal Republic of Germany.

The invention claimed is:

1. A process for scrubbing a crude mixture comprising dinitrotoluene, nitric acid, nitrogen oxides and sulfuric acid obtained in the nitration of toluene after the nitrating acid has been separated off, the process comprising:
  i) extracting in countercurrent a crude mixture with a scrubbing acid I comprising nitric acid, nitrogen oxides and sulfuric acid in a scrub comprising at least two extraction stages, such that scrubbing acid discharged from a first extraction stage (SS-I-1) of the extraction of stage i) has a total acid content of from 20 to 40% by weight, to obtain a prescrubbed crude mixture;
  ii) extracting in countercurrent the prescrubbed crude mixture comprising dinitroluene with a scrubbing acid II in a scrub comprising at least two extraction stages, such that scrubbing acid discharged from a first extraction stage (SS-II-1) of the extraction of stage ii) has a pH of less than or equal to 4 and has a content of sulfate of not more than 100 ppm, a content of nitric acid of not more than 2000 ppm and a content of nitrogen oxides (calculated as $HNO_2$) of not more than 50 ppm, to obtain a mixture comprising dinitrotoluene which is essentially free of nitric acid, sulfuric acid and nitrogen oxides.

2. The process according to claim 1, wherein the extracting i) comprises from 2 to 4 extraction stages.

3. The process according to claim 1, wherein the extracting ii) comprises from 2 to 4 extraction stages.

4. The process according to claim 1, wherein the scrubbing acid discharged from the first extraction stage (SS-II-1) of the extraction of stage ii) has a pH of from 0 to 3.

5. The process according to claim 1, wherein the scrubbing acid discharged from the first extraction stage (SS-II-1) of the extraction of stage ii) has a pH of from 0.5 to 2.

6. The process according to claim 1, wherein water or a scrubbing acid having a total acid content of from 0.2 to 1.5% by weight is fed to a last extraction stage (SS-I-n) of the extraction of stage i).

7. The process according to claim 1, wherein water is fed to a last extraction stage (SS-II-n) of the extraction of stage ii).

8. The process according to claim 1, wherein:
  I) in the first extraction stage (SS-I-1) of the extraction of stage i), the crude mixture comprising dinitrotoluene, nitric acid, nitrogen oxides and sulfuric acid is fed into a first mixer (M-I-1) together with circulated scrubbing acid (SA-I-1) from a first phase separation apparatus (S-I-1) belonging to this first extraction stage and excess scrubbing acid (SA-I-2) from the subsequent extraction stage (SS-I-2), and a scrubbing emulsion formed in the mixer is separated in the first phase separation apparatus (S-I-1) into the scrubbing acid (SA-I-1) and crude mixture which has been scrubbed once (DNT-I-1); and
  II) the crude mixture which has been scrubbed once (DNT-I-1) is, in the subsequent extraction stage (SS-I-2) of the extraction of stage i), fed into a second mixer (M-I-2) belonging to this extraction stage together with the circulated scrubbing acid (SA-I-2) from a second phase separation apparatus (S-I-2) belonging to this extraction stage and, if the extraction of stage i) comprises more than 2 extraction stages, with excess scrubbing acid (SA-I-3) from the subsequent extraction stage (SS-I-3) or, if the extraction of stage i) comprises precisely 2 extraction stages, with fresh water or scrubbing acid.

9. The process according to claim 1, wherein:
  I) in the first extraction stage (SS-II-1) of the extraction of stage ii), the prescrubbed crude mixture comprising dinitrotoluene is fed into a first mixer (M-II-1) belonging to this extraction stage together with circulated scrubbing acid (SA-II-1) from a first phase separation apparatus (S-II-1) belonging to this extraction stage and excess scrubbing acid (SA-II-2) from the subsequent extraction stage (SS-II-2), the scrubbing emulsion formed in the first mixer is separated in the first phase separation apparatus (S-II-1) into the scrubbing acid (SA-II-1) and crude mixture which has been scrubbed once (DNT-II-1); and
  II) the crude mixture which has been scrubbed once (DNT-II-1) is, in the subsequent extraction stage (SS-II-2) of the extraction of stage ii), fed into a second mixer (M-II-2) belonging to this extraction stage together with the circulated scrubbing acid (SA-II-2) from a second phase separation apparatus (S-II-2) belonging to this second extraction stage and, if the extraction of stage ii) comprises more than 2 extraction stages, with excess scrubbing acid (SA-I-3) from the subsequent extraction stage (SS-I-3) or, if the extraction of stage ii) comprises precisely 2 extraction stages, with fresh water.

10. The process according to claim 1, wherein the volume ratio of dinitrotoluene-comprising crude mixture to scrubbing acid in the extraction stages of the extraction of stage i) and the extraction of stage ii) is from 1:4 to 10:1.

11. The process according to claim 1, wherein the volume ratio of dinitrotoluene-comprising crude mixture to fresh water in the last extraction stage (S-II-n) of the extraction of stage ii) is from 1:2 to 15:1.

12. The process according to claim 1, wherein a dinitrotoluene-comprising mixture comprising a total of not more than 800 ppm of nitrocresols and nitrophenols, not more than 600 ppm of nitrobenzoic acids, not more than 300 ppm of nitric acid and nitrogen oxides, and not more than 3 ppm of sulfate is taken off from the last extraction stage (SS-II-n) of the extraction of stage ii).

13. The process according to claim 1, wherein the scrubbing acid discharged from the first extraction stage (SS-II-1) of the extraction of stage ii) has a total content of nitrocresols and nitrophenols of less than 5 ppm and a content of nitrobenzoic acids of less than 50 ppm.

14. The process according to claim 1, wherein the scrubbing acid discharged from the first extraction stage (SS-II-1) of the extraction of stage ii) is neutralized and, optionally after removal of dinitrotoluene dissolved therein by extraction and removal of the extractant, fed without further pretreatment to the biological treatment stage of a water treatment plant.

* * * * *